United States Patent [19]
Birngruber et al.

[11] Patent Number: 4,741,612
[45] Date of Patent: May 3, 1988

[54] DEVICE FOR PERFORMING A PHOTOCOAGULATION OPERATION ON A BIOLOGICAL TISSUE, ESPECIALLY ON THE FUNDUS OF AN EYE

[76] Inventors: Reginald Birngruber, No. 49, Veilchenweg, 8028 Taufkirchen; Veit-Peter Gabel, No. 8, Peter-Dorfler-Strasse, 8035 Stockdorf, both of Fed. Rep. of Germany

[21] Appl. No.: 877,823

[22] Filed: Jun. 30, 1986

Related U.S. Application Data

[63] Continuation of Ser. No. 630,989, Aug. 24, 1984, abandoned, which is a continuation of Ser. No. 274,096, Jun. 16, 1981, abandoned.

[30] Foreign Application Priority Data

Jun. 27, 1980 [DE] Fed. Rep. of Germany ....... 3024169

[51] Int. Cl.$^4$ .......................... A61B 3/10; A61B 17/36
[52] U.S. Cl. ................................. 351/221; 128/303.17
[58] Field of Search ............. 351/221; 128/395, 303.1, 128/303.17

[56] References Cited

U.S. PATENT DOCUMENTS 4,316,467 2/1982 Muckerheide ................... 128/303.1

OTHER PUBLICATIONS

J. F. Bergmann-Verlag; 74th Convention German Ophthalmological Society, Munich 1977, pp. 420-427.

Primary Examiner—John K. Corbin
Assistant Examiner—P. M. Dzierzynski
Attorney, Agent, or Firm—Cushman, Darby & Cushman

[57] ABSTRACT

A control system for use with a conventional photocoagulation device for controlling the exposure parameters of irradiation of biological tissue, such as the fundus of an eye. The photocoagulation device includes a source of radiation, a means for initiating and terminating the source of radiation, and sensing means for measuring the extent of coagulation of the biological tissue. Exposure parameters of the device include exposure time and the wavelength spot size and power of the irradiating beam. The control system cooperates with the device for determining and regulating the exposure parameters in accordance with the unique mathematical relationship between the extent and progression of coagulation during a photocoagulation operation, thereby to terminate the photocoagulation operation should unsatisfactory results be anticipated.

3 Claims, 4 Drawing Sheets

DEVICE FOR PERFORMING A PHOTOCOAGULATION OPERATION ON A BIOLOGICAL TISSUE, ESPECIALLY ON THE FUNDUS OF AN EYE

This is a continuation of application Ser. No. 630,989, filed Aug. 24, 1984, now abandoned, which in turn is a continuation application of Ser. No. 274,096 filed on June 16, 1981 now abandoned.

BACKGROUND OF THE INVENTION

This invention relates to a device for performing a photocoagulation operation on a biological tissue, especially on the fundus of an eye.

Devices of this type are known. Compare the Report of the 74th Convention of the German Ophthalmological Society (Bericht uber die 74. Zusammenkunft der Deutschen Ophthalmologischen Gesellschaft), pages 420–427, J. F. Bergmann-Verlag, Munich 1977. According to this publication, the known devices comprise a source of radiation, for example a laser, the radiation from which is concentrated on the area of tissue to be treated, and there brings about an alteration of the tissue, in particular a coagulation process. A color-change occurs during the coagulation process, in particular a white coloration, the degree of the color-change being a measure of the therapeutic effect. In order to measure the white coloration, light emitted by a second radiating device, operating under steady-conditions, is directed onto the coagulation site, and only that light of the second radiating device which is diffusely reflected at the said site is supplied to a device for measuring the radiant intensity of the reflected light. An oscilloscope, connected in series, records the change of the white coloration.

In carrying out a coagulation operation, account must be taken of the following facts. The coagulation parameters must be preset for each coagulation operation. These parameters are essentially the exposure time, the radiated power, the wavelength of the radiation, and the size of the area to be irradiated. The prior art devices include appropriate controls for adjustably setting each of these parameters before each coagulation process. However, the tissue characteristics can vary from one area to be irradiated to another such area even within the same eye. Consequently, these parameters should be adjusted in accordance with these variations in order to achieve similar effects.

Taking account of this fact, the state of the art is subject to several disadvantages which are both fundamental and practical in nature:

1. Only the coagulation operation which has already taken place is assessed, and no provision is made for intervening in the process while it is under way, or for prematurely switching off the exposure in the event of unsuitable radiation parameters. Excessively severe or excessively slight lesions can occur in the absence of a correcting intervention of this type.

2. The markedly variable tissue characteristics, which cannot be measured in vivo, make it impossible to define the "optimum coagulation parameters" prior to the coagulation operation, but if similar effects are to be obtained, account must be taken of the different tissue characteristics when selecting the coagulation parameters.

3. The variable tissue characteristics require special coagulation parameters for each individual coagulation operation, even, for example, within one eye, it being necessary to determine these parameters in advance, for each individual case, by experimental means. This experimental determination of the coagulation parameters is virtually impossible in the case of the generally large number of individual exposures in the course of a treatment (typically more than one hundred). This fact leads to the possibility that the coagulation operations may be performed too intensively.

SUMMARY OF THE INVENTION

It is, therefore, an object of the present invention to eliminate these disadvantages and to produce a device for performing a photocoagulation operation on a biological tissue, especially on the fundus of an eye, which assures a coagulation operation that is accurately matched to the conditions prevailing in each case.

These and other aspects of the invention will become more readily apparent upon review of the succeeding disclosure taken in connection with the accompanying drawings. The invention, however, is pointed out with particularity in the appended claims.

BRIEF DESCRIPTION OF THE DRAWINGS

An embodiment of the invention will now be described by way of example and with reference to the accompanying drawings in which.

DESCRIPTION OF THE PREFERRED EMBODIMENT

Figure 1A:
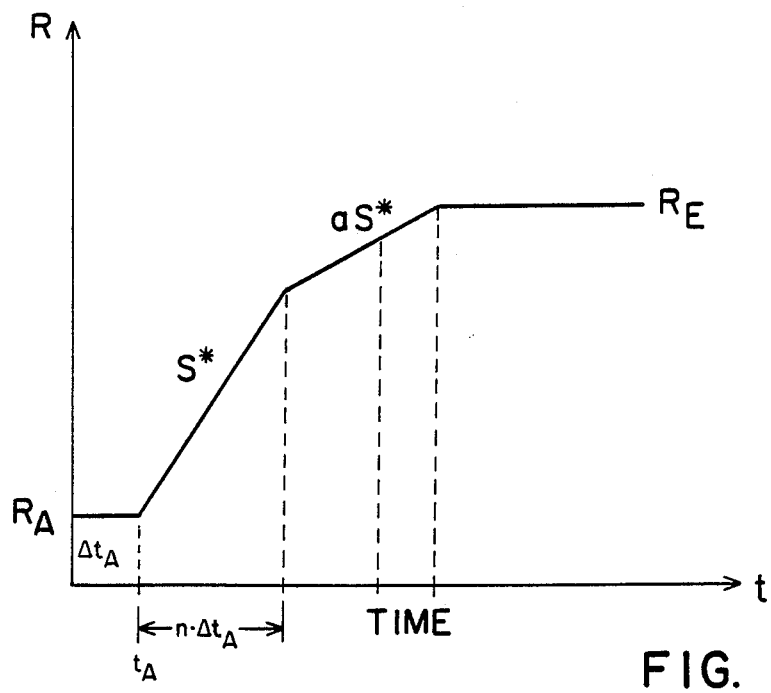
FIG. 1a is curve representing one approximation of the variation of diffusely reflected radiation R, as a function of time t.
Figure 1B:
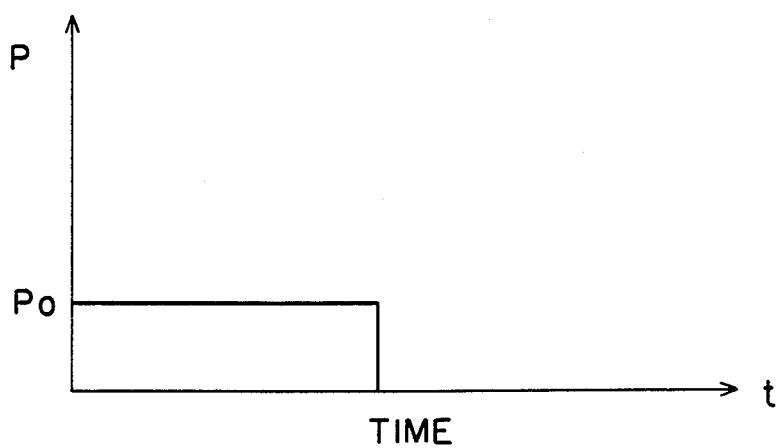
FIG. 1b is an associated graph of the power P of the coagulation radiation, as a function of time t.

In the actual case, the curve of the measured reflected radiation as a function of time starts to increase after a certain delay time during which the measured reflected radiation is substantially constant. The slope of the curve representing the increase in measured reflected radiation R rapidly increases to its maximum value at the start thereof with subsequent decrease thereof until the curve reaches saturation, i.e., approximately zero slope. FIG. 1a shows an approximation of such a curve. As shown in the approximation of FIG. 1a, for the case in which radiation is supplied over time T, at a constant power Po, the measured reflected radiation $R = R_A$ follows an approximately horizontal trace over a time $\Delta t_A$. After this delay time $\Delta t_A$, there follows an approximately linear increase of the measured reflected radiation, having the slope $S = S^*$, up to a time equivalent to n times the delay time, and thereafter an increase having a lower slope $aS^*$. The factors n and a can be determined experimentally. They are dependent on the size of the area irradiated, but are independent, within wide limits, of the radiated power supplied. Finally, the diffuse reflection value R gradually approaches the saturation value $R_E$ which for the sake of simplicity is shown in FIG. 1a as a straight line section. The transition to the value $R_E$ takes place with a delay $\Delta t_E$ after switching off the radiation Po which effects the coagulation process.

It has now been found that the value $\Delta t_A$ has a relationship fixed with respect to the slopes $S^*$ and $aS^*$, and also with respect to the saturation value $R_E$, so that it is sufficient to determine $\Delta t_A$ in order to be able, thereafter, to predict, substantially, the further course of the curve $R=f(t)$.

Figure 2:
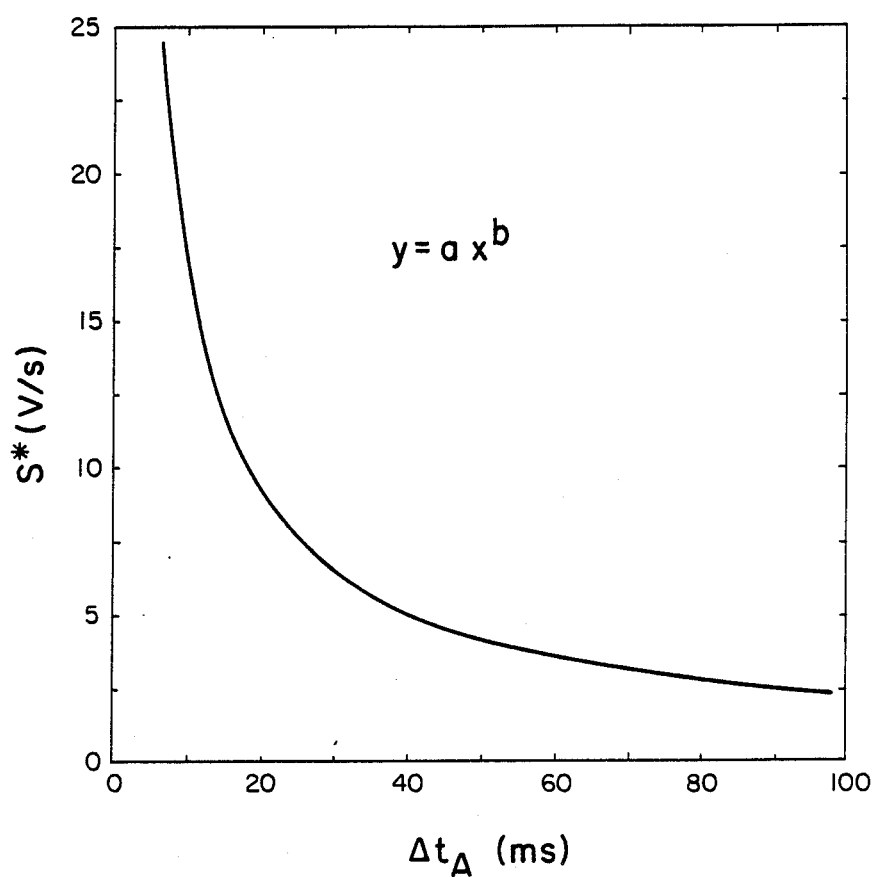
FIG. 2 is a curve showing the relationship between slope $S^*$ as a function of the delay time $\Delta t_A$, based on actual measurements.

The relationship $S^*=f(\Delta t_A)$ is illustrated in FIG. 2, a curve resembling a hyberbola being the result, thus implying that the product $\Delta t_A \times S^*$ is approximately constant. It is thus sufficient to determine $\Delta t_A$ in order to be able, thereafter, to recognize immediately whether the value which is to be expected for $R_E$ will be correct, or whether it will be unsuitable, that is to say, too low or too high. It is therefore possible to influence the course of the coagulation process during the initial phases thereof, i.e., while it is still developing, and, to alter the exposure parameters, and in particular to reduce the degree of coagulation, to switch off completely, and/or to perform repetitive coagulation operations.

The following equation then applies for the exposure time T in the case of the approximation represented by FIG. 1a:

$$T = \frac{\Delta R}{aS^*} - \frac{(1+n)\Delta t_A}{2a} + n \Delta t_A$$

According to this relationship, the necessary exposure time T is already fixed shortly after the start of the exposure (at the point in time $$\frac{1+n}{2} \Delta t_A).$$

If $T > T_{max.}$, and/or $E > E_{max.}$, E being the radiation energy supplied and $T_{max.}$ and $E_{max.}$ being the maximum permissible values, the exposure is immediately terminated by automatic means, and only a slight degree of damage occurs in the irradiated area. The desired degree of coagulation is achieved, using the preset parameters, by successively increasing the power and by repeated exposures (this process can also be effected automatically).

Figure 3:
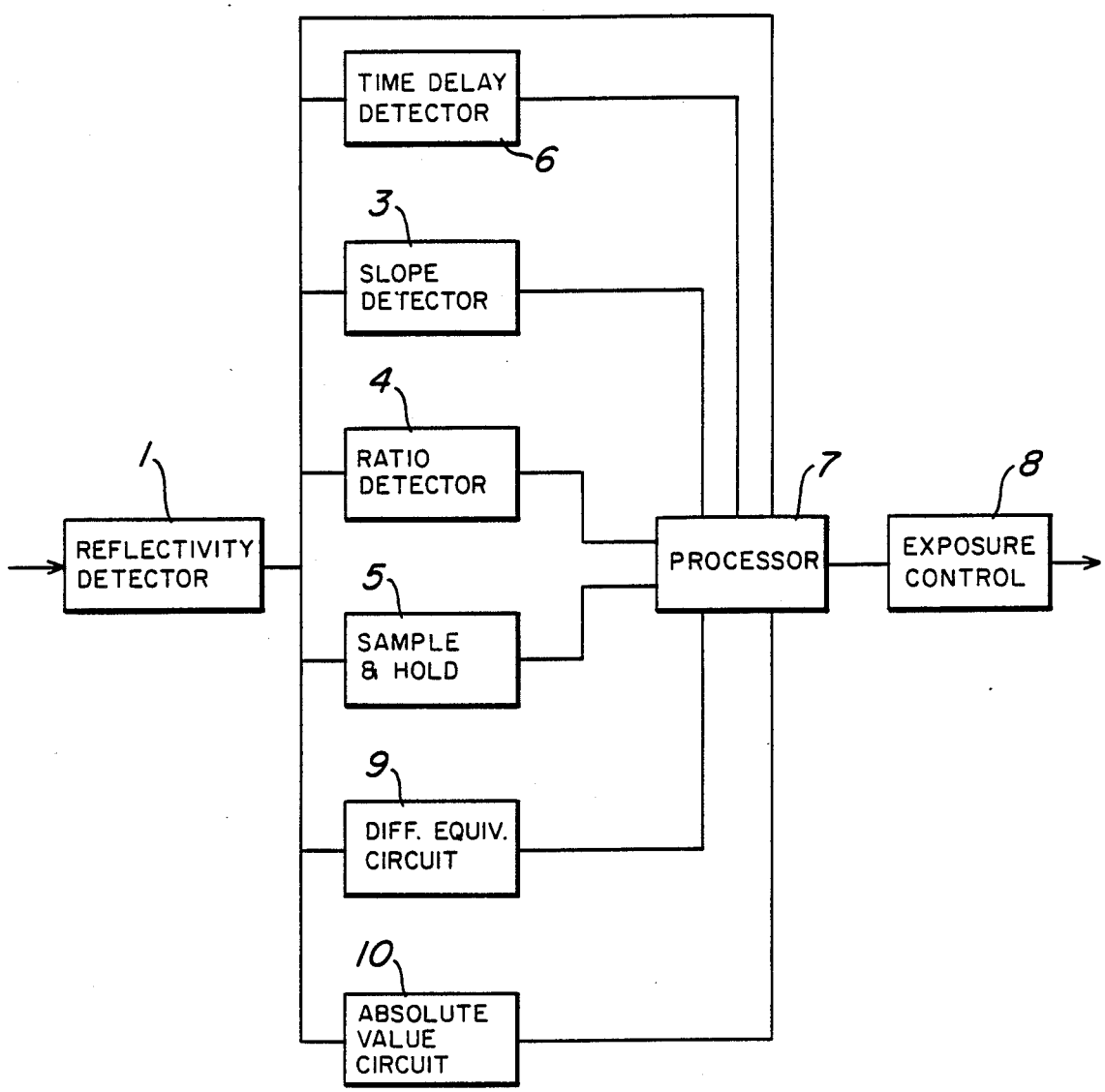
FIG. 3 is a block diagram of a device according to the invention.

The delay time $\Delta t_A$ is determined by means of a conventional device 6 for measuring this delay time (FIG. 3). However, it is also possible to determine the degree of the coagulation from the slope S of the curve $R=f(t)$, or from the ratio of an instantaneous diffuse reflection value R to the initial value $R_A$, instead of from $\Delta t_A$, and to control the exposure parameters by reference to S or $R/R_A$. A differentiator 3 serves to measure the slope S, while the above-mentioned ratio of the diffuse reflection values is formed with the aid of a ratio-forming circuit 4 which comprises a memory circuit for retaining the initial value $R_A$ with which subsequent values of R are compared. It is also sufficient, under some circumstances, to effect the control of the exposure parameters with the aid of an absolute diffuse reflection value R, this value being measured at a selectable point in time by means of a conventional sample/hold amplifier circuit 5. The circuit 9 thereby provides a signal representing the difference equivalent to the measured diffuse reflected radiation less the initial measured diffuse reflected radiation $(R-R_A)$ while the circuit 10 produces a signal representing the absolute value of the measured diffuse reflected radiation and block 8 contains a conventional control circuit for controlling the exposure parameters.

Not only can each of the circuits 3, 4, 5, 6, 9, 10, illustrated in FIG. 3, be installed independently, but it is also possible to arrange for two or more of these circuits to be connected in parallel. In this case, a logic circuit 7 is needed in order to logically combine the output signals of the individual circuits which are used, for the purpose of generating a control signal which is a function of all the output signals.

Given, as expressed above, the following equation for exposure time T of the high energy laser in one simplified example:

$$T = \frac{\Delta R}{aS^*} - \frac{(1+n)\Delta t_A}{2a} + n \Delta t_A \qquad (1)$$

and, as also expressed above, the relationship $$S^* \cdot \Delta t_A \approx K \qquad (2)$$

where K is a constant or, when rewritten $$\Delta t_A \cong \frac{K}{S^*} \qquad (3)$$

$$S^* \cong \frac{K}{\Delta t_A} \qquad (4)$$

the exposure time T can also be expressed solely as a function of $\Delta t_A$ or S as follows:

$$T(\Delta t_A) = \frac{\Delta R \cdot \Delta t_A}{aK} - \frac{(1+n) \cdot \Delta t_A}{2a} + n \Delta t_A \qquad (5)$$

$$T(S) = \frac{\Delta R}{aS^*} - \frac{(1+n) \cdot K}{2aS} + \frac{nK}{S^*} \qquad (6)$$

$$T = \frac{\Delta R_{norm}}{aS_{norm}} - \frac{(1+n)\Delta t_A}{2a} + n \Delta t_A \qquad (7)$$

where $R_{norm}=\Delta R/R_A$ and $S_{norm}=S/R_A$.

Figure 4:
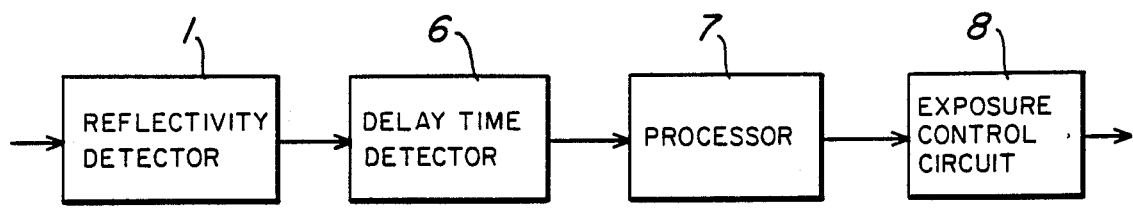
FIG. 4 is a functional block diagram representing a simplified mode of operation of the embodiment illustrated in FIG. 3.
Figure 5:
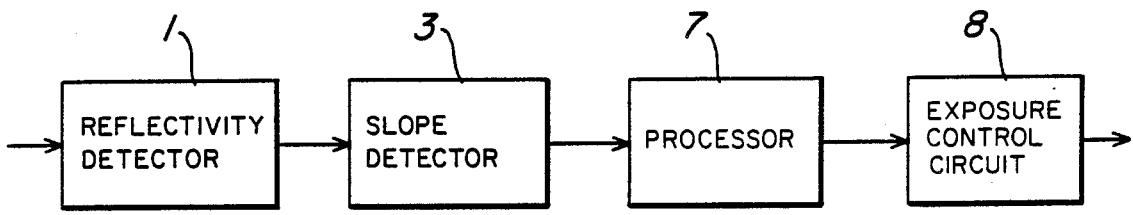
FIG. 5 is a functional block diagram representing another simplified mode of operation of the embodiment illustrated in FIG. 3.
Figure 6:
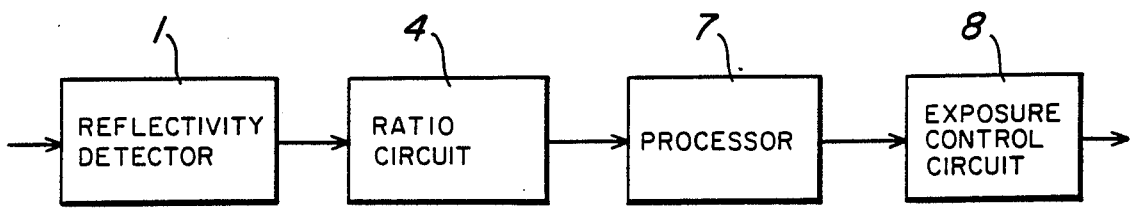
FIG. 6 is a functional block diagram representing a still further simplified mode of operation of the embodiment of FIG. 3.

FIGS. 4, 5 and 6 show some of the possible systems for controlling the parameters of a conventional photocoagulation device when utilizing some of circuits of FIG. 3 independently with the processor 7, instead of being connected all in parallel, as shown in FIG. 3. In FIG. 4, a conventional time delay detector 6 receives the reflected measured radiation R from the detector 1 in the photocoagulation device, and supplies a delay time $\Delta t_A$ to the processor 7 which, in turn, computes the exposure parameters according to a predetermined equation, such as, for instance, equation 5. The processor 7 then effects control of the exposure control circuit 8 in the photocoagulation device to continue or terminate the exposure of the fundus.

In FIGS. 5 and 6, on the other hand, the slope detector 3 and ratio circuit 4 supply corresponding signals to the processor 7 to control the treating laser according to a predetermined equation such as, for example, equation (1).

In contrast to the state of the art, provision may also be made, if appropriate, to construct the device 1 for measuring the reflected intensity to be mobile so that it can be employed not only for picking up the diffuse reflection at different angles, but also for measuring the radiation which is transmitted through the treated tissue in parts of the human body where this is possible. This can be realized, for example, with the aid of flexible light guides placed underneath the tissue to be treated.

The need for a second source of radiation is eliminated by an arrangement in which a device 10 for determining the absolute value of the diffuse reflection R and a control element 8 for the exposure parameters are connected in series.

Since the cirucit used in the various parts of the block diagram of FIG. 3 are of known conventional type, forming no part of the present invention, a detailed description thereof is dispensed with herein for the sake of simplicity.

The invention may be embodied in other specific forms without departing from the spirit of essential characteristics thereof. The embodiment is therefore to be considered in all respects as illustrative and not restrictive.

We claim:

1. A control system for controlling a source of radiation of a photocoagulation device for photocoagulating biological tissue, said device including means to produce a beam of said source having predetermined spot size, and means for varying exposure parameters of said source including at least one of power regulating means for regulating the power of said source, spot size regulating means for varying the spot size of said beam, exposure time regulating means for varying the exposure time of said source, and wavelength varying means for varying the wavelength of said source, which system comprises:

control means including reflectively sensing means for measuring light reflected from said tissue to sense the level of coagulation of the tissue and means responsive to said reflectivity sensing means for controlling, during the photocoagulation process, at least one of said power regulating means, spot size regulating means, wavelength varying means and exposure time regulating means according to a given relationship, in which, during an initial delay time phase of said relationship, the measured reflected light is substantially constant, which is followed by an initial significant increase in measured reflected light that eventually reaches a saturation level, and wherein said given relationship is dependent on at least one of said delay time, the slope of said increase in measured reflected light, the difference equivalent in measured reflected light between R and $R_A$, and the ration of $R/R_A$, where R is the instantaneous value of measured reflected light along the curve of the increase in measured reflected light and $R_A$ is the measured reflected light during said delay time.

2. A control system as recited in claim 1 wherein said control means includes several circuit means operatively connected in parallel, a first one of said circuit means determining the slope of said increase, a second one of said circuit means determining the quotient of the instantaneous value R along the curve of said increase and the value $R_A$, a third one of said circuit means for storing R, a fourth one of said circuit means for determing the delay time, a fifth one of said circuit means for determining the difference between R and $R_A$, and a sixth one of said circuit means for storing a predetermined value of the measured reflected light.

3. A control system as recited in claim 2, wherein an output of all of said parallel connected circuit means are operatively connected with a logic circuit means operable to control at least one of said parameters.

* * * * *